| (12) | United States Patent | (10) Patent No.: | US 8,048,883 B2 |
|---|---|---|---|
| | Amala et al. | (45) Date of Patent: | Nov. 1, 2011 |

(54) POLYMORPHIC FORM OF IMATINIB MESYLATE AND A PROCESS FOR ITS PREPARATION

(75) Inventors: Kompella Amala, Hyderabad (IN); Thungathurthi Srinivasa Rao, Hyderabad (IN); Bhujanga rao Adibhatla Kali Satya, Hyderabad (IN); Sreenivas Rachakonda, Hyderabad (IN); Nannapaneni Venkaiah Chowdary, Hyderabad (IN); Khadgapathi Podili, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 952 days.

(21) Appl. No.: 10/585,702

(22) PCT Filed: Nov. 16, 2004

(86) PCT No.: PCT/IN2004/000352
§ 371 (c)(1),
(2), (4) Date: Jan. 24, 2008

(87) PCT Pub. No.: WO2005/077933
PCT Pub. Date: Aug. 25, 2005

(65) Prior Publication Data
US 2008/0255138 A1    Oct. 16, 2008

(30) Foreign Application Priority Data
Feb. 11, 2004  (IN) .............................. 105/CHE/2004

(51) Int. Cl.
*A01N 43/58* (2006.01)
*A61K 31/50* (2006.01)
*C07D 239/02* (2006.01)

(52) U.S. Cl. ......... 514/247; 544/242; 544/315; 544/330
(58) Field of Classification Search .................. 544/242, 544/315, 330; 514/247
See application file for complete search history.

(56) References Cited

FOREIGN PATENT DOCUMENTS

| EP | 0 564 409 A1 | | 6/1993 |
|---|---|---|---|
| WO | WO 99/03854 | * | 1/1999 |
| WO | WO 2004/074502 A2 | | 9/2004 |
| WO | WO 2004/106326 A1 | | 12/2004 |

OTHER PUBLICATIONS

Third party observations for corresponding EP application No. 04806748.2 mailed on Feb. 2, 2011.
Office Action for corresponding EP application No. 04806748.2 mailed on Feb. 7, 2011.

* cited by examiner

*Primary Examiner* — Paul V. Ward
(74) *Attorney, Agent, or Firm* — Merchant & Gould P.C.

(57) ABSTRACT

This invention discloses a novel stable crystal form of imatinib mesylate, designated by us as $\alpha_2$ Form, which is stable at room temperature and even at higher temperatures up to 120° C. and accelerated stress conditions and, freely soluble in water. This invention also discloses a pharmaceutical composition containing the novel stable $\alpha_2$ form of Imatinib mesylate and other usually employed excipients, useful in the treatment of Chronic Myelogenous Leukemia (CML). This new $\alpha_2$ Form of imatinib mesylate is prepared by slurrying Imatinib base in isopropanol at room temperature followed by addition of methane sulfonic acid and maintaining 50-60 ° C. followed by filtration. This invention also discloses another process for the preparation of the novel, stable $\alpha_2$ crystalline form of Imatinib Mesylate by the conversion of Imatinib mesylate β-polymorphic modification by suspending it in water and organic solvents, distilling off water azeotropically, cooling and filtering to obtain the $\alpha_2$ crystal form.

7 Claims, 8 Drawing Sheets

POLYMORPHIC FORM OF IMATINIB MESYLATE AND A PROCESS FOR ITS PREPARATION

FIELD OF INVENTION

Figure 1:
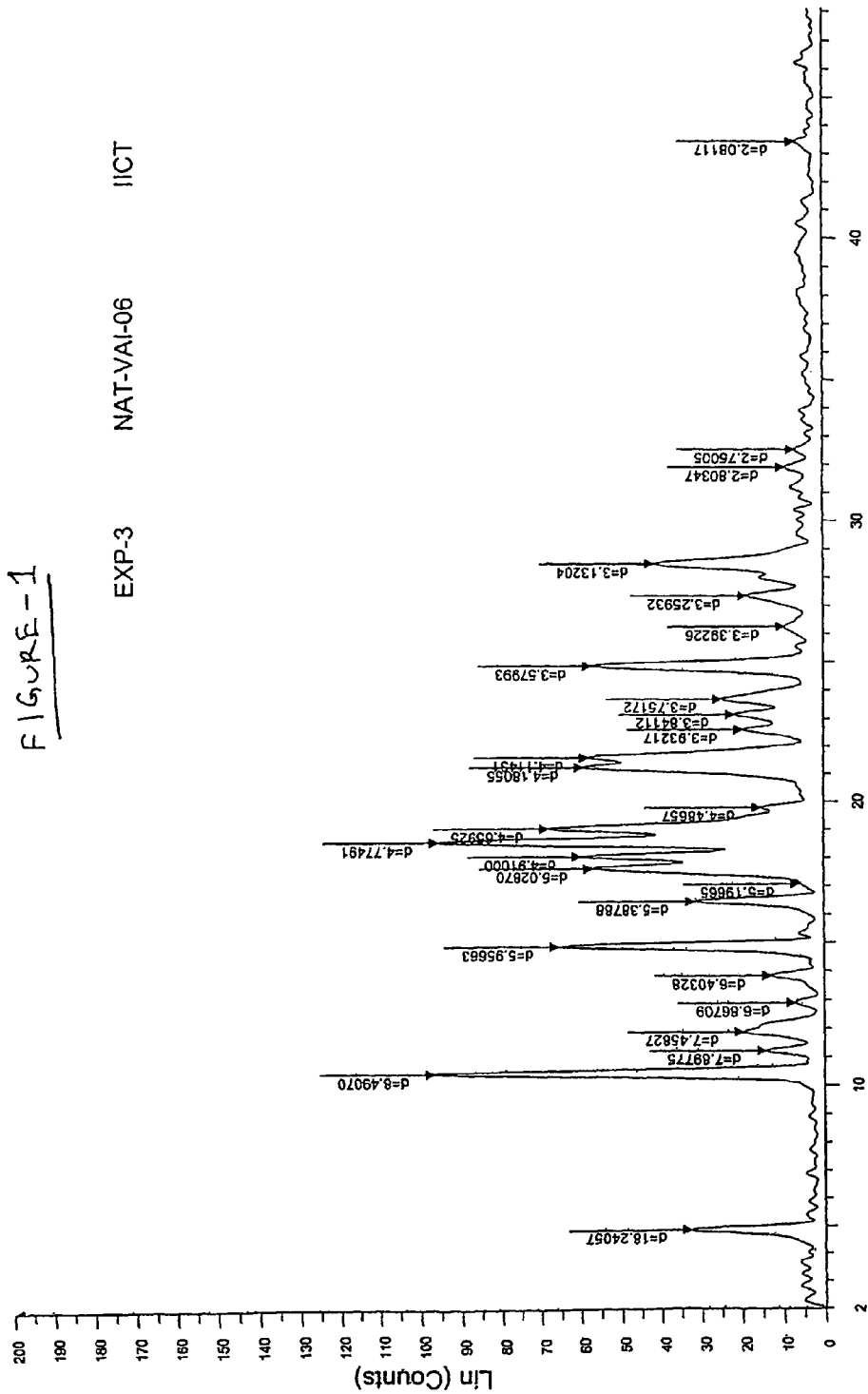

The invention provides a novel, polymorphic form of Imatinib mesylate and a process for its preparation. The novel, polymorphic form of Imatinib mesylate, which is designated by us as $\alpha_2$, is stable at room temperature and even at higher temperatures up to 120° C. and accelerated stress conditions and freely soluble in water.

The present invention also relates to a process for the preparation of the novel polymorphic form and pharmaceutical compositions containing the novel stable $\alpha_2$ form of Imatinib mesylate and usually employed excepients useful in the treatment of Chronic Myelogenous Leukemia (CML). The Imatinib mesylate has the formula given below

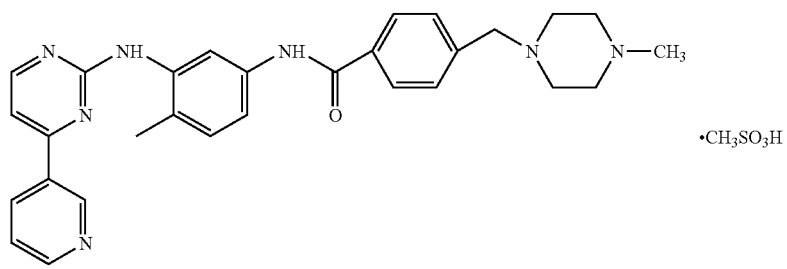

BACKGROUND OF THE INVENTION

Imatinib mesylate which is N-{5-[4-(4-methylpiperazinomethyl)-benzoylamido]-2-methylphenyl}-4-(3-pyridyl)2-pyrimidine-amine, having the formula given above is approved under the trademark "Gleevec®" by the US Food and Drug Administration for the treatment of Chronic Myelogenous Leukemia before and after the failure of interferon alpha. It has also been approved for the treatment of patients with kit (CD117) positive unresectable and/or metastatic malignant Gastro Intestinal Stromal Tumors (GISTs). Recently it has been approved for the treatment of pediatric patients with Philadelphia chromosome positive (Ph+) Chronic Myeloid Leukemia (CML) in chronic phase. It is known that Imatinib mesylate exists in two polymorphic forms α and β (WO 99/03854).

In the said WO application it has been sated that the α form prepared is needle shaped and is hygroscopic. It has also been stated that in this form the crystals are not well suited for pharmaceutical formulations as solid dosage from because their physical properties for example, their flow characteristics are unfavorable. The applicants have also mentioned that under certain conditions however, it is possible to obtain a crystal form which is not needle shaped. This form, in the above patent is named as βform.

From the above given description regarding the α form it is very clear that the α form of Imatinib mesylate is not suitable for preparing formulations due to its: unsuitable physical characteristics and the form which is used is only the β form.

The said WO application also describes processes for the preparation of both the forms of Imatinib Mesylate. In the Examples 1 to 3 of the said patent the process for the preparation of Imatinib mesylate β-form has described using a maximum of 50 gms Imatinib base in solution.

In the Example-2 of the said patent a process has been described for the preparation of the β-form which involves suspending Imatinib base in methanol, adding methane sulfonic acid in methanol, heating to 50° C., followed by carbon treatment and distilling off methanol. Then dissolving the residue in minimum methanol and inoculation by some seeding crystals of Imatinib mesylate β-form.

The said WO application also describes processes for the preparation of both the forms of Imatinib Mesylate In the Example-1 of the said WTO application, the α-crystal form is prepared as follows:

Imatinib base was suspended in ethanol, methane sulfonic acid was added and heated under reflux for 20 minutes and than filtered at 65° C. The filtrate was evaporated down to 50% and the residue filtered off at 25° C. (filter material A). The mother liquor was evaporated to dryness. The residue and filter material A were suspended in ethanol dissolved under reflux with addition of water. Cooling overnight to 25° C., filtration and drying yielded Imatinib mesylate α-crystal form.

The above process for preparing α-crystal form suffers from the following disadvantages a) In Examples 2 and 3 seed crystals of β-form are required to crystallize out the product
b) The process for preparing α-crystal form given under Example-1 is not reproducible. Repetition of the experiment exactly under identical conditions as reported in the above patent (WO 99/03854) resulted only in the α-form
c) Thus, there is currently no available process to prepare the α-crystal modification.

Important solid state properties of a pharmaceutical substance are its rate of dissolution in aqueous fluid. The rate of dissolution of an active ingredient in a patients stomach fluid may have therapeutic consequences because it imposes an upper limit on the rate at which an orally-administered active ingredient may reach the blood stream. The solid state form of a compound may also affect its behavior on compaction and its storage stability.

These practical physical characteristics are influenced by the conformation and orientation of molecules in the unit cell, which defines a particular polymorph form of a substance. The polymorphic form may give rise to thermal behavior different form that of the amorphous material (or) another polymorphic form.

Thermal behaviour is measured in the laboratory by such techniques as capillary melting point, Thermo Gravimetric Analysis (TGA) and Differential Scanning Calorimetry (DSC), and may be used to distinguish some polymorphic forms from others. A particular polymorphic form may also give rise to distinct properties that may be detectable by X-Ray Powder Diffraction (XRPD) solid state $^{13}$CNMR spectrometry and infrared spectrometry.

The various characteristics and properties of the polymorphic forms of a substance. e.g. shape, colour, density and the like, will make one polymorphic form preferable over the others for production and/or pharmaceutical compounding. As a result, a very first step in the processes of product development of a new pharmaceutical agent is the determination of whether it exists in polymorphic forms and if so which of such form possesses advantages for the eventual commercial pharmaceutical application. In the case of Imatinib mesylate, β form is offered commercially under the trade name Gleevec®/Glivec®.

In the patent mentioned above (WO 99/03854), β-form was selected over α-form based on the following observations and conclusions.
(i) β-form is thermodynamically stable at room temperature and at temperatures below 140° C. Greater stability of the β form is thus expected.
(ii) (β-crystal form is less hygroscopic than the α-crystal form.
(iii) α-crystal form is meta stable at room temperature
(iv) β-crystal has the advantage that its flow properties are substantially more favourable than those of that the α-crystal form.

Based on the above information, we undertook a detailed study of the solid state physical properties of the polymorphic forms of Imatinib mesylate. The presumption was that these properties may be influenced by controlling the conditions under which Imatinib mesylate is obtained in solid form.

Our detailed studies by carrying out research and development work on polymorphic forms of Imatinib Mesylate, and their processes for preparation surprisingly revealed the existence of another novel, stable polymorphic form of imatinib mesylate which we have designated as $\alpha_2$ form, having the below mentioned characteristics.

The novel $\alpha_2$ form of the present invention, can be prepared under certain specific conditions with improved physical properties such as greater stability and less hygroscopicity etc thereby making it suitable just like the β-form for commercial pharmaceutical applications.

Accordingly, we focussed our R&D efforts in taking up an elaborate study on the polymorphism of Imatinib Mesylate with particular reference to stable forms. Our detailed studies of the novel $\alpha_2$ form revealed that:
i. The novel $\alpha_2$-form is not meta stable and is stable at room temperature and even at higher temperatures like 120° C.
ii. The novel $\alpha_2$-form is stable at normal and accelerated stress conditions both in bulk and formulated capsule form.
iii. The novel $\alpha_2$-form is as freely soluble in water as is the β-form. The rate of dissolution of the $\alpha_2$-form in the formulation is comparable and even better than that of the β-form.
iv. The flow properties of the formulations prepared with the $\alpha_2$ form and β-forms are comparable as the same excipient composition is employed in both cases.

The above mentioned stable $\alpha_2$ form of imatinib Mesylate is not hither to known and is a novel polymorphic form. In addition, the form prepared by us now is also suitable for developing a pharmaceutical composition. Such a pharmaceutical composition containing $\alpha_2$ form is also not known and is novel.

Therefore, the main objective of the present invention is to provide a novel $\alpha_2$ crystalline form of Imatinib Mesylate which is stable at room temperature and even at higher temperatures like 120° C. and accelerated stress conditions, freely soluble in water and having the characteristics given in Table 1 given below Another objective of the present invention is to provide a process for the preparation of novel $\alpha_2$ form of Imatinib Mesylate which is stable and less hygroscopic and water soluble having the characteristics given in Table 1

Yet another objective of the present invention is to provide a pharmaceutical composition useful for the treatment of Chronic Myeloid Leukemia containing the novel $\alpha_2$ form of Imatinib Mesylate which is stable and less hygroscopic and water soluble having the characteristics given in table 1.

Still another objective of the present invention is to provide an improved process for the preparation of β-polymorphic Imatinib mesylate.

Accordingly, the present invention provides a novel $\alpha_2$ crystalline form of Imatinib Mesylate which is stable at room temperature and even at higher temperatures up to 120° C. and accelerated stress conditions, freely soluble in water having the XRD characteristics given in the Table-I below.

TABLE I

| Angle [2-Theta] | d-value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |
| 28.475 | 3.13204 | 42.4 |
| 31.896 | 2.80347 | 9.0 |
| 32.533 | 2.75005 | 6.6 |
| 43.447 | 2.08117 | 6.4 |

According to another embodiment of the present invention there is provided a process for the preparation novel $\alpha_2$ crystalline form of Imatinib Mesylate which is stable at room temperature and even at higher temperatures like 120° C. and accelerated stress conditions, freely soluble in water and having the characteristics given in Table 1 which comprises suspending Imatinib base in isopropanol and adding methane sulfonic acid at room temperature and maintaining the reaction mixture at a temperature in the range of 40-80° C., for a period in the range of 20-30 minutes, cooling and filtering to obtain the $\alpha_2$ crystal form.

According to yet another embodiment of the invention there is provided another process for the preparation of novel $\alpha_2$ crystalline form of Imatinib Mesylate which comprises converting Imatinib mesylate β-polymorphic modification which comprises suspending β-polymorphic it in water and organic solvents like methanol, Isopropyl ether, toluene, cyclohexane and Isopropyl alcohol, distilling off water azeotropically and, cooling filtering to obtain the $\alpha_2$ crystal form.

According to stiff another embodiment of the present invention, there is provided a pharmaceutical composition useful for the treatment of Chronic Myeloid Leukemia which comprises novel $\alpha_2$ form of Imatinib Mesylate which is stable and less hygroscopic and water soluble having the characteristics given in table 1 and a commonly employed pharmaceutically acceptable excipients.

According to another embodiment of the present invention there is provided an improved process for the preparation of β-polymorphic form of Imatinib mesylate which comprises suspending Imatinib base in a solvent selected from acetone, acetonitrile, mixture of methanol and isopropanol and mixture of isopropanol and water and adding methane sulfonic acid to the resulting solution at room temperature and maintaining the solution at the reflux temperature of the solvent (or) at room temperature and filtering the β-crystal form.

It is to be noted that the $\alpha_2$ form of Imatinib mesylate prepared by the process of the present invention does not substantially convert over time to form β, either as such in bulk form or after formulation in the dosage form, upon storage at about 40° and about 75% relative humidity for at least about 6 months.

Determination of presence of imatinib mesylate form-β in Imatinib mesylate $\alpha_2$-form prepared by the process of the present invention may be made by analysis for the presence of various peaks associated with form-β particularly at 9.7, 13.9, 18.2, 20.0, 20.6, 21.1, 22.1, 22.7, 23.8, 29.8, 30.8±0.2 degree 2θ. (WO99/03854).

FIG. 1 of the drawings accompanying these specifications shows the X-Ray Powder Diffraction (XRPD) pattern which substantially depicts a typically pure sample of Imatinib Mesylate of $\alpha_2$-form prepared by the process disclosed in the Example-1 given below. The 2θ values and intensities are tabulated in Table-1.

The other figures correspond to the data as detailed below:—

Figure 2:
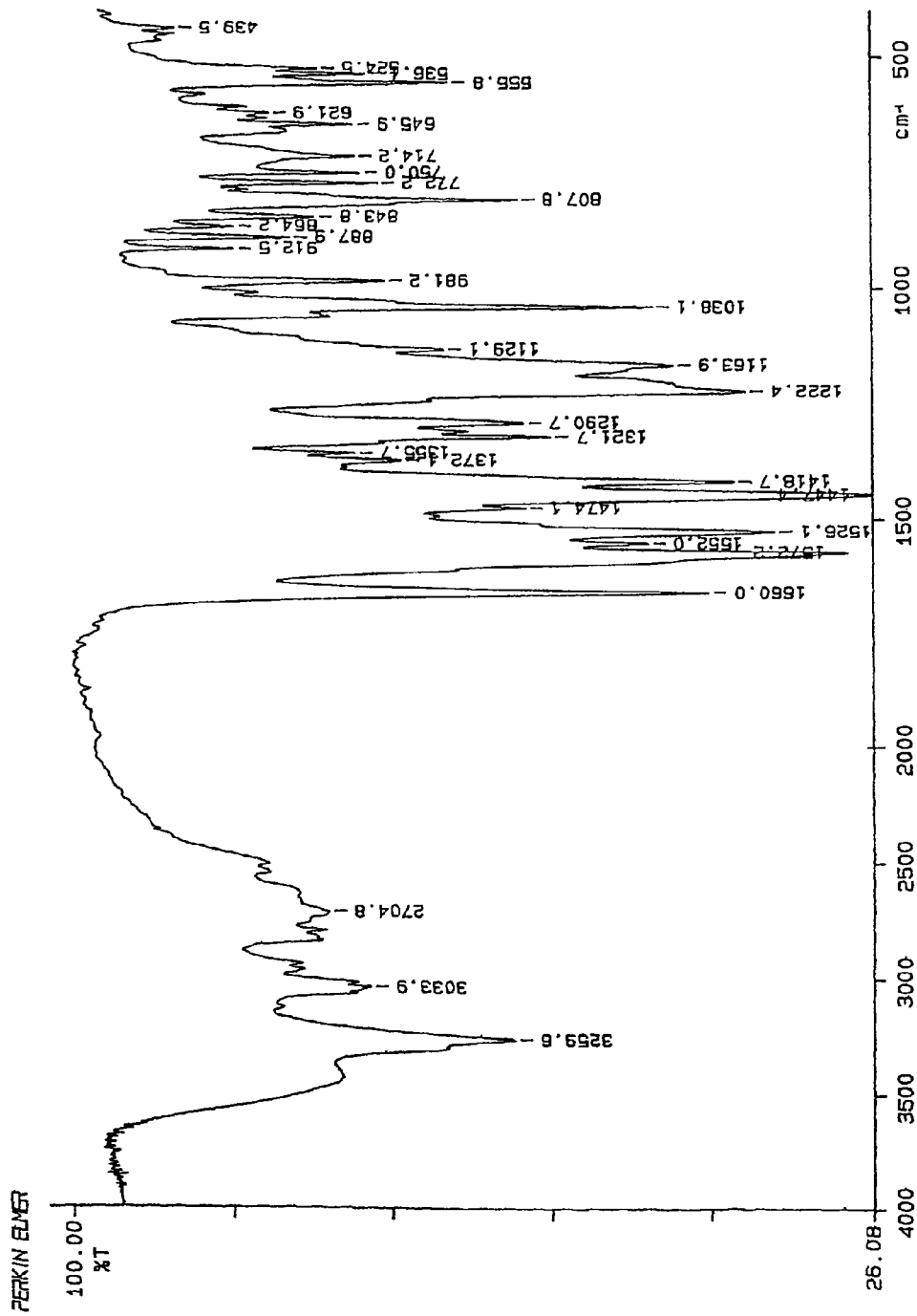
Figure 3:
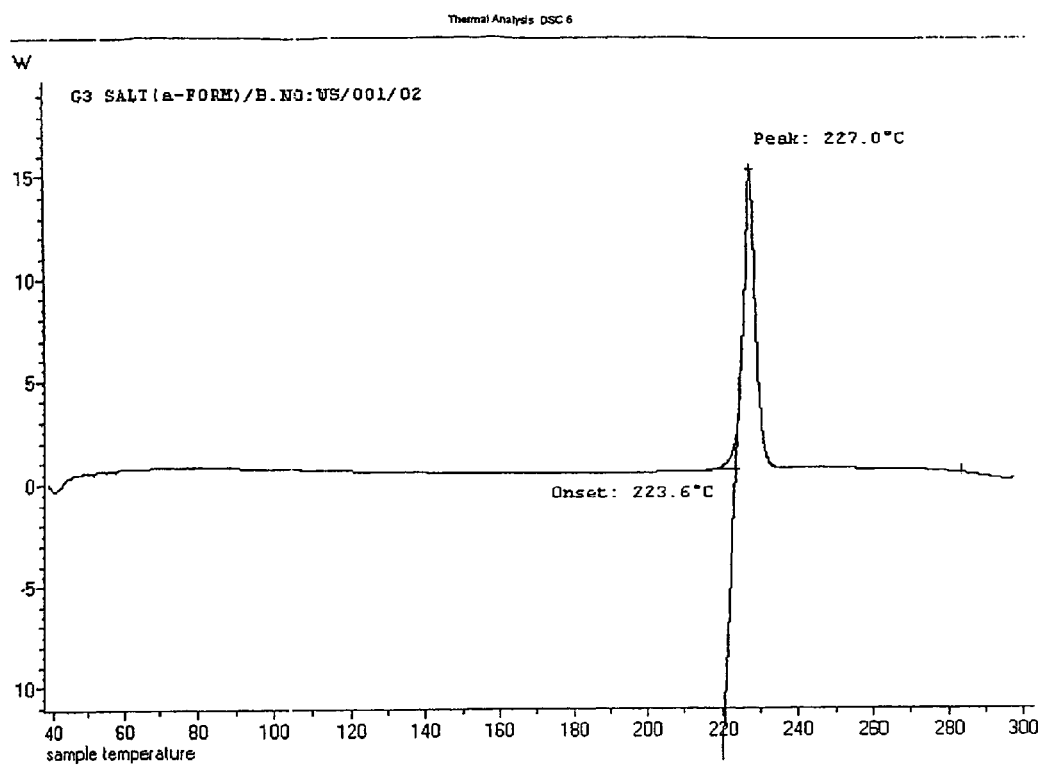
Figure 4:
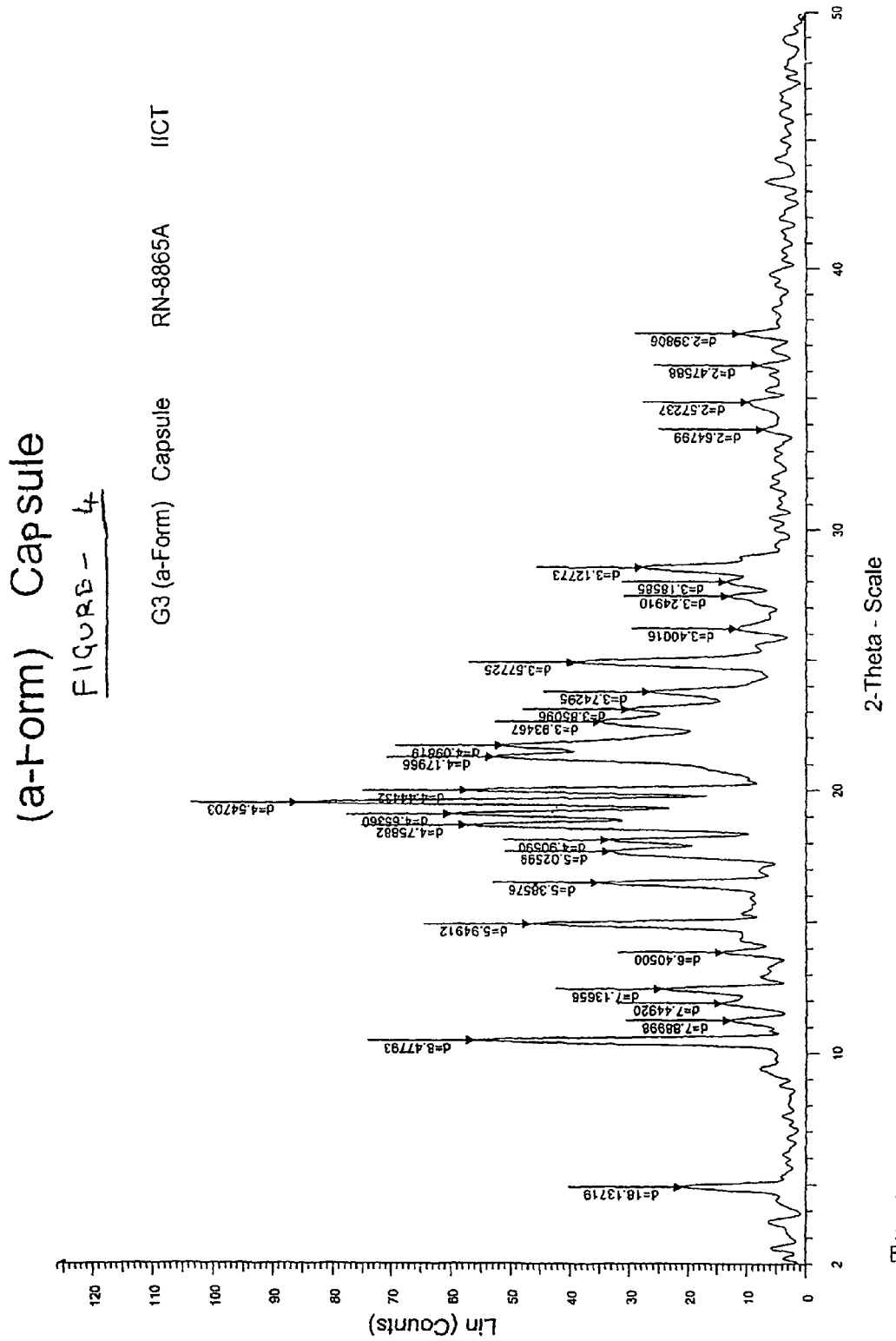
Figure 5:
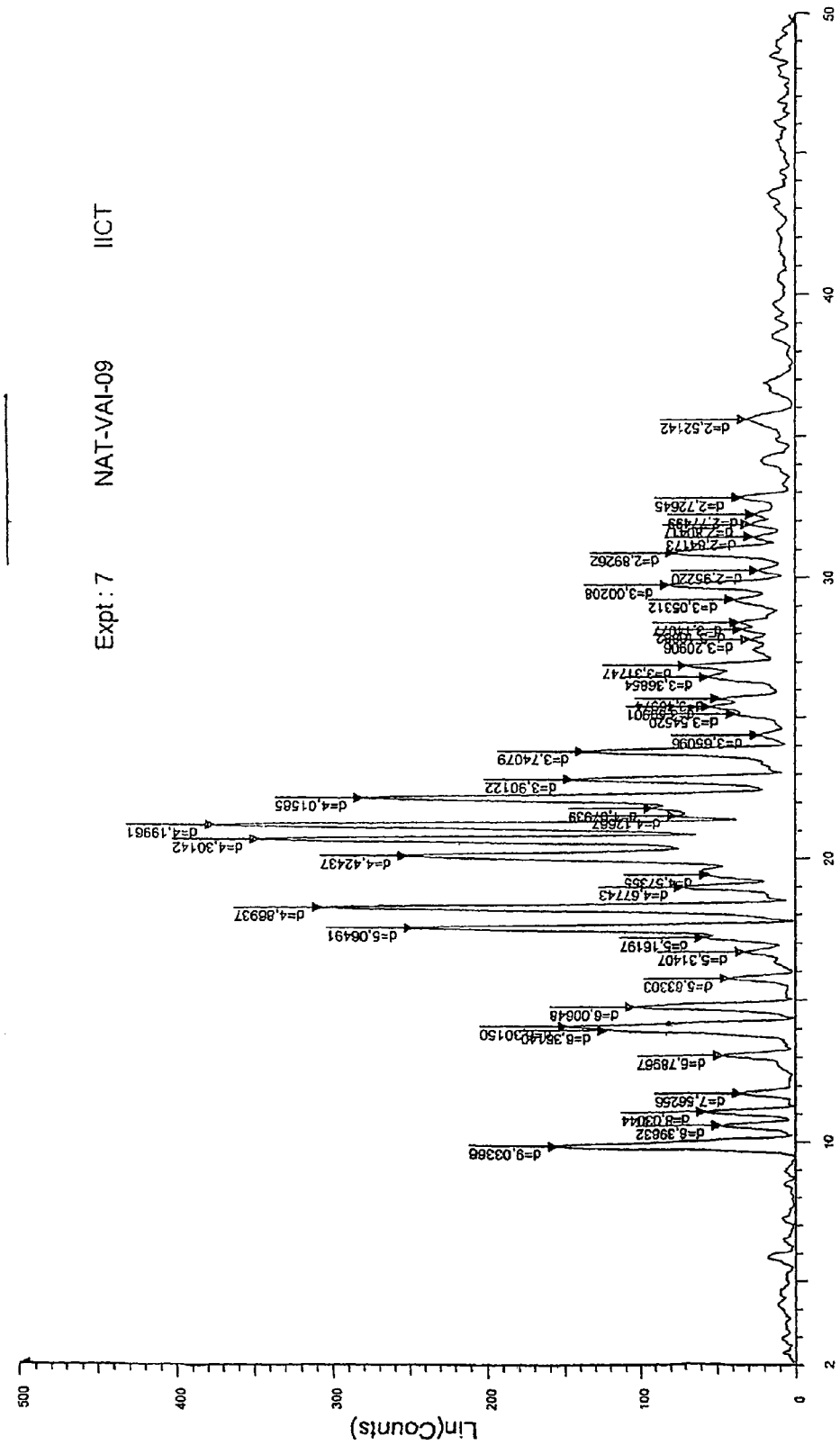
Figure 6:
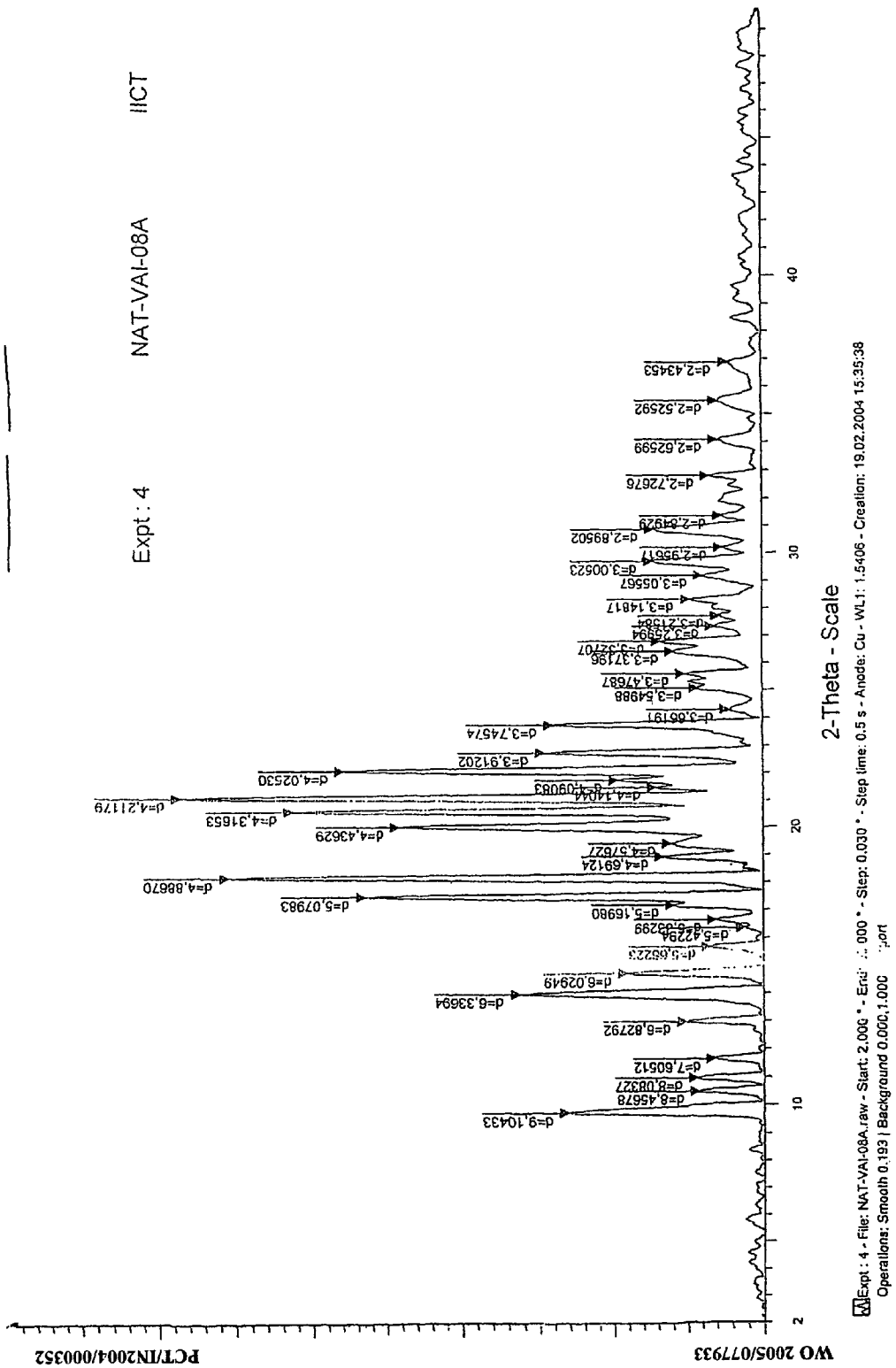
Figure 7:
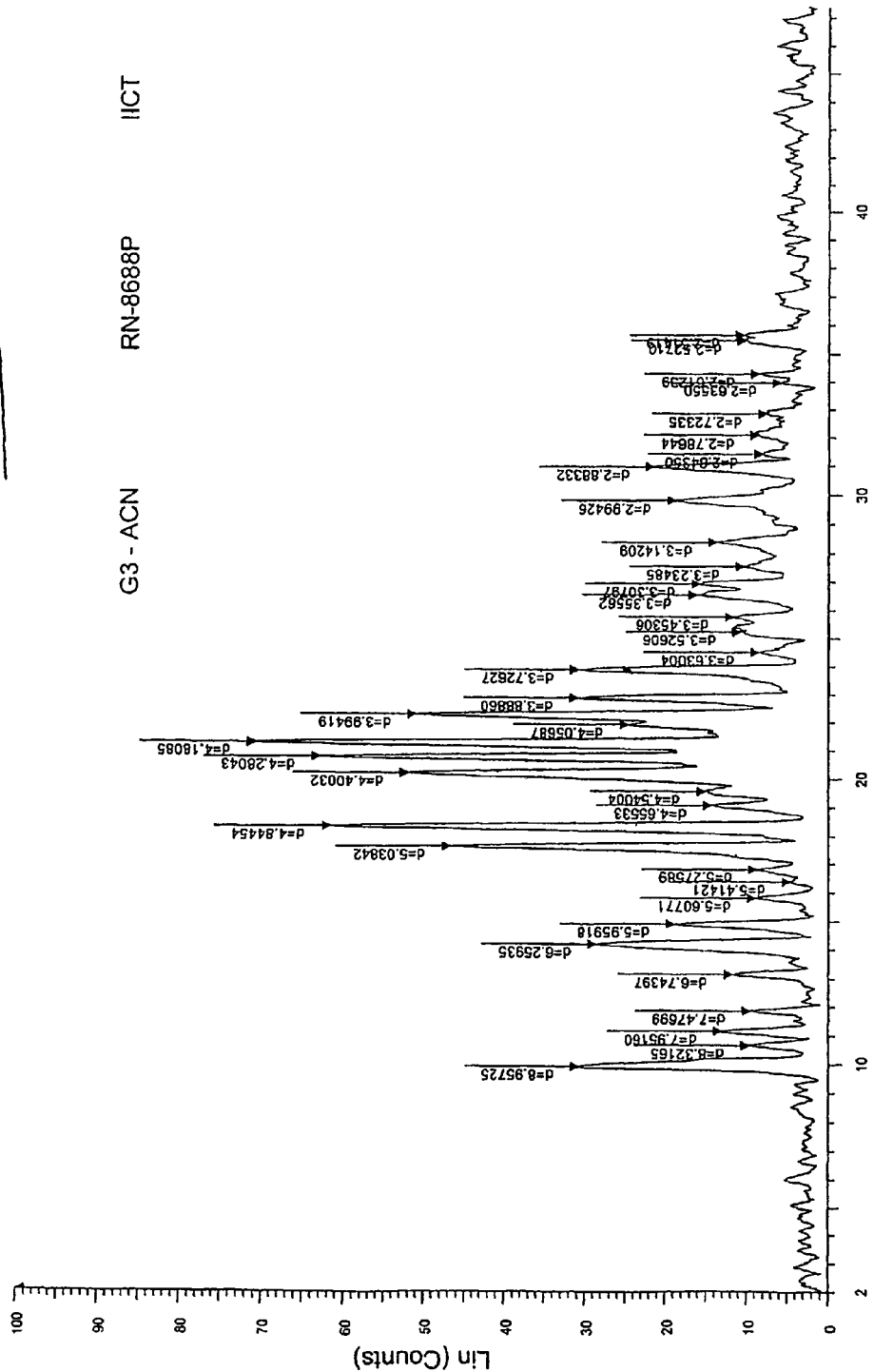
Figure 8:
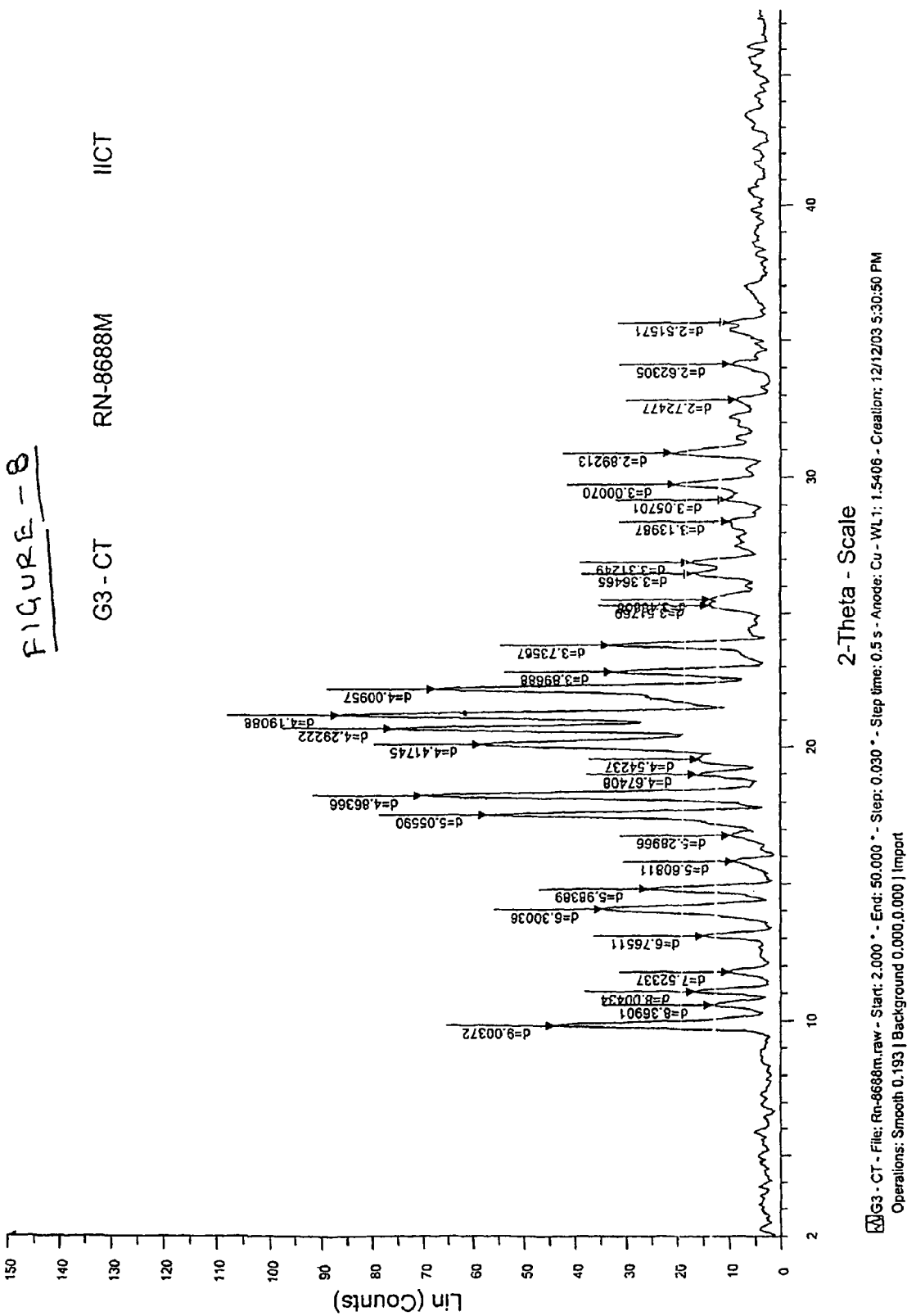

FIG. - 1 XRD spectrum of the novel $\alpha_2$ form
FIG. - 2 IR spectrum of the novel $\alpha_2$ form
FIG. - 3 DSC thermogram of the novel $\alpha_2$ form
FIG. - 4 XRD spectrum of the novel $\alpha_2$ form capsules stored for 6 months at 40° ± 2°/75 ± 5% (Table-5)
FIG. - 5 XRD spectrum of β form prepared by he process of the invention
FIG. - 6 XRD spectrum of β form form prepared by he process of the invention
FIG. - 7 XRD spectrum of β form form prepared by he process of the invention
FIG. - 8 XRD spectrum of β form form prepared by he process of the invention The dosage form of the formulation containing the novel, stable $\alpha_2$ form prepared by the process of the present invention, preferably oral dosage form, may be a capsule containing the composition preferably a powdered on granulated solid composition, within either a hard (or) soft shell. The shell may be made from gelatine and optionally contains a plasticizer such as glycerin and sorbitol and an opacifying agent (or) colorant.

Methods known in the art, may be used to prepare the pharmaceutical composition containing Imatinib mesylate $\alpha_2$ form in the form of capsules. The excipients which may be employed include micro crystalline cellulose, lactose, crospovidone XL, colloidal silicondioxide magnesium stearate and talc Table-2 shows suitable ranges of active ingredients and excipients (weight %) and the preferred amounts for the present pharmaceutical formulations.

TABLE 2

Pharmaceutical compositions containing Imatinib Mesylate $\alpha_2$-form

| S. No. | Material | Range of % composition (w/w) | Preferred % composition | Function |
|---|---|---|---|---|
| 1. | Imatinib mesylate $\alpha_2$-form | 45-60% | 53 | Active ingredient |
| 2. | Micro crystalline cellulose | 15-25% | 21 | Filler and disintegrant |
| 3. | Lactose | 10-20% | 13 | Diluent |
| 4. | Crospovidone XL | 5-10% | 8.7 | Disintegrant |
| 5. | Magnesium stearate | 1-2% | 1.3 | Lubricant |
| 6. | Talc | 0.5-1.0% | 0.80 | Glidant |
| 7. | Colloidal Silicon dioxide | 1.5-2.5% | 2.20 | Glidant |

Table-3 shows two typical examples of the capsule formulation containing Imatinib Mesylate $\alpha_2$-form and their dissolution and stability characteristics.

TABLE 3

PHARMACEUTICAL COMPOSITIONS CONTAINING IMATINIB MESYLATE $\alpha_2$-FORM
Dissolution and stability characteristics

| Material | Composition (%) B. No. 001 | Composition (%) B. No. 002 |
|---|---|---|
| Imatinib mesylate $\alpha_2$-form | 50 | 53 |
| Microcrystalline cellulose | 25 | 21 |
| Lactose | 12 | 13 |
| Crosporidone XL | 6 | 8.7 |
| Magnesium stearate | 1.5 | 1.3 |
| Talc | 0.5 | 0.80 |
| Colloidal silicon dioxide | 2.0 | 2.2 |
| Dissolution rate | 85% (10 min) 90% (20 min) 100% (45 min) | 85% (10 min) 90% (20 min) 100% (45 min) |
| Stability | 1. stable at 40° ± 2° C. and 75 ± 5% RH 2. stable at 25° ± 2° C. and 60 ± 5% RH | 1. stable at 40° ± 2° C. and 75 ± 5% RH 2. stable at 25° ± 2° C. and 60 ± 5% RH |

Inference: Two typical batch formulations of Imatinib $\alpha_2$-form are prepared. The dissolution and stability characteristics indicate that $\alpha_2$-form has excellent formulation characteristics.

Table-4 shows the heat stability of $\alpha_2$ form over the temperature range 110-120° C. The $\alpha_2$ form is shown to be non-metastable and stable when heated at 120° C. for 6 hours.

Stability of $\alpha_2$-Crystal Form

Pure $\alpha_2$-crystal polymorph 1 gm prepared by the process described in Example 1 was taken in a boiling test tube and heated gradually in oil bath the substance was examined by XRPD. The results are tabulated below

TABLE 4

| Polymorph content* before hating | Temperature | Time of heating (hours) | Polymorph form detected* after heating |
|---|---|---|---|
| $\alpha_2$ form | 110° C. | 2 | $\alpha_2$ form |
| $\alpha_2$ form | 110° C. | 4 | $\alpha_2$ form |
| $\alpha_2$ form | 120° C. | 2 | $\alpha_2$ form |
| $\alpha_2$ form | 120° C. | 4 | $\alpha_2$ form |
| $\alpha_2$ form | 120° C. | 6 | $\alpha_2$ form |

*The presence of form-β was below the detection level in these examples.

Inference: The $\alpha_2$ form of Imatinib mesylate is not metastable.

It is fairly stable to heat even at 120° C./6 hours.

Table-5 shows the stability of $\alpha_2$ form under accelerated stress conditions (45±2° C., 75±5% RH, 6 months) in the bulk and capsule formulation

TABLE 5

Stability of $\alpha_2$ form of Imatinib mesylate in bulk and formulated capsule

| Polymorph content* of imatinib mesylate in formulated capsule Polymorph form detected | Polymorph content* of bulk imatinib mesylate Polymorph form detected | Duration of storage (months) at 40 ± 2° C./75 ± 5% RH |
|---|---|---|
| $\alpha_2$ form | $\alpha_2$ form | 0 Month |
| $\alpha_2$ form | $\alpha_2$ form | 1 Month |
| $\alpha_2$ form | $\alpha_2$ form | 2 Months |
| $\alpha_2$ form | $\alpha_2$ form | 3 Months |
| $\alpha_2$ form (XRPD FIG. - 4) | $\alpha_2$ form | 6 Months |

*The presence of form-β was below the detection level in these examples showing that $\alpha_2$ form is not converted to β-form over a time period. The stability of $\alpha_2$ form in bulk and in the formulated capsule is thus established.

Table-6 shows comparative dissolution data of Imatinib capsule formulation containing $\alpha_2$ form and β-form. The formulation with $\alpha_2$ form is found to have better dissolution characteristics.

TABLE 6

Comparative dissolution data for Imatinib mesylate capsules 100 mg* ($\alpha_2$ and β-forms)

| Test parameters | |
|---|---|
| 1. Dissolution medium | 0.1 N HCl |
| 2. Dissolution volume | 900 ml |
| 3. RPM (Revolutions Per Minute) | 50 |
| 4. Wave length (for assay determination) | 240 nm |

TABLE 6-continued

Comparative dissolution data for Imatinib mesylate capsules 100 mg* ($\alpha_2$ and β-forms)

| Release profile | Imatinib mesylate (β-crystal form) capsules 100 mg | Imatinib mesylate ($\alpha_2$ crystal form) capsules 100 mg |
|---|---|---|
| 5 minutes | 32.6% | 61.3% |
| 10 minutes | 54.4% | 85.5% |
| 15 minutes | 69.4% | 90.5% |
| 20 minutes | 78.2% | 92.6% |
| 30 minutes | 95.8% | 98.0% |
| 45 minutes | 100.0% | 100.0% |

The capsules contain Imatinib Mesylate equivalent of 100 mg of Imatinib base. The excipients are as per the Example-7

Inference: The release profile and dissolution data show that the capsule formulation with $\alpha_2$-form is better than the formulation with β-form.

Storage of capsule containing pure Imatinib mesylate $\alpha_2$ form prepared by the process of the present invention at about 40° C. and about 75% relative humidity for 6 months, does not show any significant conversion to β-polymorphic form of Imatinib mesylate preferably less than about 5%. The detection of Imatinib mesylate form-β in a pharmaceutical formulation to the extent about 1% w/w or more may be accomplished by use of x-ray powder diffraction.

The pharmaceutical formulations containing the novel, stable $\alpha_2$ form prepared by the process of the present invention are useful in the treatment of Chronic Myelogenous Leukemia. The oral pharmaceutical dosage forms preferably contain about 100 mg of the base equivalent.

The preparative aspects, physical and functional properties of novel Imatinib mesylate $\alpha_2$ form prepared by the process of the present invention are compared with the properties of α form described in the prior art (WO 99/03854) and tabulated in Table-7. The tabulated data clearly demonstrates the stability and functional superiority of the novel $\alpha_2$ polymorph of the present invention over the α polymorph described in WO 99/03854.

TABLE 7

A COMPARATIVE ACCOUNT OF IMATINIB MESYLATE α-FORM KNOWN IN PRIOR ART AND THE NOVEL $\alpha_2$ FORM OF CURRENT INVENTION

| S. No. | Property | Literature α form WO 99/03854 | Present invention $\alpha_2$ form |
|---|---|---|---|
| 1. | Method of preparation | Preparation reported in ethanol solvent. However method not reproducible yielding β-form only | The method results in novel and stable $\alpha_2$ form consistently in high purity and yield. |
| 2. | Melting point | 226° C. | 223-227° C. |
| 3. | Differential scanning thermogram | 226° C. (start of melting) | 225-227° C. Peak 227° |
| 4. | XRD | Spectrum scan given 2θ values not listed | Spectra given in FIGS. 1 & 4 Principal 2θ values 4.9, 10.4, 14.9, 16.4, 17.6, 18.6, 19.1, 21.2, 24.6, 24.9, 28.5 |
| 5. | Crystal shape | Needle shape (Not free flowing) | Non-needle shaped free-flowing crystals |
| 6. | Hygroscopicity | Hygroscopic | Non-hygroscopic |
| 7. | Dissolution characteristic | Not mentioned | Dissolves freely in water Dissolution of more than 95% during 30 min in capsule formulation |
| 8. | Flow properties | Not well-suited to pharmaceutical solid dosage forms | Found to be well suited for pharmaceutical formulations as solid dosage forms. |

TABLE 7-continued

A COMPARATIVE ACCOUNT OF IMATINIB MESYLATE α-FORM
KNOWN IN PRIOR ART AND THE NOVEL $\alpha_2$ FORM OF CURRENT
INVENTION

| S. No. | Property | Literature α form WO 99/03854 | Present invention $\alpha_2$ form |
|---|---|---|---|
| 9. | Stability | Metastable at room temperature | Stable at room temperature and even at 120° C. |

The details of the invention are provided in the Examples given below which are provided to illustrate the invention only and therefore they should not be construed to limit the scope of the invention.

EXAMPLE-1

Preparation of Novel Imatinib Mesylate Form-α 2 in Lab Scale

Imatinib base (200 gms) obtained directly from the synthesis was suspended in 2.5 L of isopropanol. Methane sulfonic acid (38.9 gms) in 400 ml anhydrous Isopropanol was added slowly during 20 minutes at room temperature. Reaction mass was heated to 75-80° C. for 30 minutes and slowly cooled to 40-45° C. during 45 minutes. Filtered at 40-45° C. and washed with 250 ml Isopropanol. The wet cake was dried for 6 hours at 80° C. The yield was 170 gms (71%)

Melting range—226-227° C. (DSC)

The FIG. 1 of the drawings accompanying this specification shows the X-Ray Powder Diffraction (XRPD) pattern which substantially depicts a typically pure sample of Imatinib mesylate of form-$\alpha_2$ prepared as per the process disclosed in this Example The 2θ values and intensities are tabulated in Table-1.

FIG. 2 shows the IR spectrum of $\alpha_2$ form prepared by the process described in this Example FIG. 3 shows the DSC thermogram of $\alpha_2$ form prepared by the process described in this Example FIG. 4 shows the XRD spectrum of $\alpha_2$ form from capsules stored for 6 months at 40°±2°/75±5% (Table-5)

EXAMPLE-2

Preparation of Novel Imatinib Mesylate Form-α 2 on Industrial Scale

Imatinib base (10 Kg) obtained directly from the synthesis was suspended in 125 L of Isopropanol. Methane sulfonic acid (1.94 Kg) in 20 L Isopropanol was added slowly during 40-60 minutes at room temperature. Reaction mass was heated to 75-80° C. for 30 minutes and slowly cooled to 40-45° C. during 45 minutes. Filtered at 40±45° C. and washed with 12 L Isopropanol. The wet cake was dried for 6 hours at 80° C. The yield was 8.6 Kg (72%)

Melting range—225-226° C. (DSC)

XRPD, IR matches Standard $\alpha_2$ form as given in Example-1 above

EXAMPLE-3

Preparation of Imatinib Mesylate Forms from β-Form 100 gms of imatinib mesylate β-polymorphic modification was suspended in 40 ml of water and 1.0 L of methanol. Distilled off water and methanol completely under vacuum during 1 hour. 600 ml of isopropyl alcohol was charged at 70° C. and seeded with pure $\infty_2$ crystal. Reaction mass was brought to room temperature during 15 minutes and stirred at the same temperature for 15 minutes. Filtered and washed with 100 ml Isopropyl alcohol. Dried in oven at 50-60° C. under vacuum.

Yield—95 gms.

Melting range—224.2-226.8

XRPD, IR matches Standard $\alpha_2$ form as given in Example-1 above

EXAMPLE-4

Preparation of Imatinib Mesylate Form-$\alpha_2$ from β-Form 100 gms of imatinib mesylate β-polymorphic modification was suspended in 300 ml of water and 2.0 L of cyclohexane. Water was distilled azeotropically along with 1 L cyclohexane during 2 hours. The reaction mass was brought to room temperature during 15 minutes, stirred at the same temperature for 30 minutes. Filtered and washed with 100 mlcyclohexane. Dried in oven at 50-60° C. under vacuum.

Yield—80 gms.

Melting range—222-224.8° C.

XRPD, IR matches Standard $\alpha_2$ form as given in Example-1 above

EXAMPLE-5

Preparation of Imatinib Mesylate Form-$\alpha_2$ from β-Form 100 gms of imatinib mesylate β-polymorphic modification was suspended in 300 ml of water and 1.5 L of toluene Water was distilled azeotropically along with 750 ml toluene during 2 hours. 750 ml of isopropyl alcohol was charged at 40° C. and the reaction mass was brought to room temperature during 15 minutes stirred at the same temperature for 15 minutes. Filtered and washed with 50 ml toluene. Dried in oven at 50-60° C. under vacuum.

Yield—90 gms.

Melting range (DSC)—222-224.8° C.

XRPD, IR matches Standard $\alpha_2$ form as given in Example-1 above

EXAMPLE-6

Preparation of Imatinib Mesylate form-$\alpha_2$ from β-Form 100 gms of imatinib mesylate β-polymorphic modification was suspended in 300 ml of water and 2.0 L of isopropyl ether. Water was distilled azeotropically along with 1 L Isopropyl ether during 2 hours. The reaction mass was brought to room temperature during 15 minutes, stirred at the same temperature for 30 minutes. Filtered and washed with 100 ml Isopropyl ether. Dried in oven at 50-60° C. under vacuum.

Yield—52 gms.

Melting range (DSC)—222-225.1° C.

XRPD, IR matches Standard $\alpha_2$ form as given in Example-1 above

EXAMPLE-7

Preparation of Imatinib Mesylate Form-1 in Isopropanol: Methanol Mixture

Imatinib base (0.5 Kg) was suspended in 6 L of isopropanol at room temperature. Methane sulfonic acid (97.2 gms) in 1 L isopropanol was added slowly during 30 minutes. Reaction mass was heated to 80-85° C. and 2.5 L of methanol was added through the condenser at reflux temperature. Maintained for 6 hours at 70-75° C. and slowly brought to RT during 1 hour. Filtered and washed with mixture of isopropanol. (1.5 L) and methanol (0.5 L). Dried for 6 hours at 65° C. The yield was 0.51 Kg (85%)

Melting range—215-217° C. (DSC)

XRPD spectrum as given in FIG. 5

XRPD matches standard β-form

EXAMPLE-8

Preparation of Imatinib Mesylate Form-β in Acetone with Heating

Imatinib base (0.25 Kg) was suspended in 12 L of acetone Methane sulfonic acid (48.6 gms) in 0.5 L acetone was added slowly during 30 minutes at room temperature. The reaction mass was heated to reflux temperature for 30 minutes and was slowly brought to room temperature during 45 minutes. Filtered and washed with 1 L acetone and dried for 6 hours at 65° C. The yield was 255 gms (85%)

Melting range—215-217° C. (DSC)

XRPD spectrum as given in FIG. 6

XRPD matches standard β-form

EXAMPLE-9

Preparation of Imatinib Mesylate Form-β in Acetone at Room Temperature

Imatinib base (0.25. Kg) was suspended in 12 L acetone. Methane sulfonic: acid (48.6 gms) in 0.5 L acetone was added slowly during 30 minutes at room temperature. The suspension was stirred at room temperature for 1 hour. Filtered and washed with 1 L acetone and dried for 6 hours at 65° C. The yield was 270 gms (90%)

Melting range—207-212° C. (DSC)

XRPD matches standard β-form

EXAMPLE-10

Preparation of Imatinib Mesylate Form-β in Acetonitrile with Heating

Imatinib base (0.25 Kg) was suspended in 12 L acetonitrile. Methane sulfonic acid (48.6 gms) in 0.5 L acetonitrile was added slowly during 30 minutes at room temperature. The reaction mass was heated to reflux temperature for 30 minutes and was slowly brought to room temperature slowly during 45 minutes. The suspension was stirred at room temperature for 1 hour. Filtered and washed with 1 L acetonitrile and dried for 6 hours at 65° C. The yield was 260 gms (86.6%)

Melting range—208-211° C. (DSC)

XRPD spectrum as given in FIG. 7

XRPD matches standard β-form

EXAMPLE-11

Preparation of Imatinib Mesylate Form-β in Acetonitrile at Room Temperature

Imatinib base (0.25 Kg) was suspended in 12 L acetonitrile. Methane sulfonic acid (48.6 gms) in 0.5 L acetonitrile was added slowly during 30 minutes at room temperature. The suspension was stirred at room temperature for 3 hours. Filtered and washed with 1 L acetonitrile and dried for 6 hours at 65° C. The yield was 265 gms (88.0%)

Melting range—211-215° C. (DSC)

XRPD matches standard β-form

EXAMPLE-12

Preparation of Imatinib Mesylate Form-β in Isopropanol and Water

Imatinib base (0.5 Kg) was suspended in 6 L of isopropanol. Methane sulfonic acid (97.2 gms) in 0.5 L DM water was added slowly during 30 minutes. The reaction mass was maintained over night at room temperature under stirring. Filtered and washed with mixture of Isopropanol and water, dried for 6 hours at 65° C. The yield was 0.41 Kg (68%)

Melting range—210-216° C. DSC

XRPD spectrum as given in FIG. 8

XRPD matches standard β-form

EXAMPLE-13

Preparation of Imatinib Mesylate Form-β in Methanol and Methylene Chloride

Imatinib base (0.1 Kg) was suspended in 0.8 L of methanol. Methane sulfonic acid (19.4 gms) in 0.2 L methanol was added slowly during 20 minutes. Reaction mass was heated to reflux temperature for 30 minutes. Distilled off methanol completely under reduce pressure. Charged 0.3 L methylene chloride to the residue and stirred 3 hours at room temperature. Filtered and washed with 0.2 L Methylene chloride and dried for 5 hours at 65° C. The yield was 0.1 Kg (83%)

Melting range—216.6° C. (DSC)

XRPD matches standard β-form

EXAMPLE-14

Capsules containing 120 mg of active ingredient of the compound prepared by the process described in the Example-1 and having the following composition are prepared by dry blending in customary manner.

| S. No | Ingredients | mg/capsule |
|---|---|---|
| 1. | Active ($\alpha_2$ form) | 120* |
| 2. | Microcrystalline cellulose | 50 |
| 3. | Lactose | 30 |
| 4. | Crospovidine | 20 |
| 5. | Colloidal silicon dioxide | 5 |

-continued

| S. No | Ingredients | mg/capsule |
|---|---|---|
| 6. | Magnesium stearate | 3 |
| 7. | Talc | 2 |

Average weight: 230 mg/capsule
*Equivalent to 100 mg
The pharmaceutical formulations containing the novel, stable $\alpha_2$ form prepared by the process of the present invention are useful in the treatment of Chronic Myelogenous Leukemia.

ADVANTAGES OF THE INVENTION

1. The stable $\alpha_2$-polymorphic form of imatinib mesylate is new and not known hitherto before
2. The novel $\alpha_2$-polymorphic form of Imatinib mesylate produced is stable and compares well with the β-polymorphic form in stability.
3. The novel $\alpha_2$ form prepared is suitable for pharmaceutical applications which was hitherto not possible
4. The process produces novel stable $\alpha_2$ polymorphic form of imatinib mesylate consistently.
5. The process results in the preparation of a stable dosage form (capsule) incorporating the novel $\alpha_2$ polymorph form.
6. Provides improved process for the manufacture of β-polymorphic form on an industrial scale

We claim:
1. An $\alpha_2$ crystalline form of Imatinib Mesylate which has the XRPD characteristics given below

| Angle 2-Theta | d Value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |
| 28.475 | 3.13204 | 42.4 |
| 31.896 | 2.80347 | 9.0 |
| 32.533 | 2.75005 | 6.6 |
| 43.447 | 2.08117 | 6.4 | which is sufficiently stable that it retains these XRPD characteristics after 6 hours at 120° C. and/or after 6 months at about 40° C. and about 75% relative humidity; and which is a solid in the form of free flowing crystals that are not needle shaped.

2. A process for the preparation of an $\alpha_2$ crystalline form of Imatinib Mesylate, the process comprising:
  suspending Imatinib base in isopropanol;
  adding methane sulfonic acid at room temperature;
  maintaining the reaction mixture at a temperature of 40-80° C. for 20-30 minutes, and
  cooling to 40-45° C. and filtering to obtain the $\alpha_2$ crystal form;
  wherein the $\alpha_2$ a crystal form has the XRPD characteristics given below,

| Angle 2-Theta | d Value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |
| 28.475 | 3.13204 | 42.4 |
| 31.896 | 2.80347 | 9.0 |
| 32.533 | 2.75005 | 6.6 |
| 43.447 | 2.08117 | 6.4 | is sufficiently stable that it retains these XRPD characteristics after 6 hours at 120° C. and/or after 6 months at about 40° C. and about 75% relative humidity; and is a solid in the form of free flowing crystals that are not needle shaped.

3. A process for the preparation of an $\alpha_2$ crystalline form of Imatinib Mesylate, the process comprising:
  suspending β polymorphic form Imatinib Mesylate in water and an organic solvent, the organic solvent comprising methanol, Isopropyl ether, toluene, cyclohexane, or Isopropyl alcohol;
  distilling off water azeotropically; and
  cooling and filtering to obtain the $\alpha_2$ crystal form;
  wherein the $\alpha_2$ crystal form has the XRPD characteristics given below,

| Angle 2-Theta | d Value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |

-continued

| Angle 2-Theta | d Value Angstrom | Intensity % |
|---|---|---|
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |
| 28.475 | 3.13204 | 42.4 |
| 31.896 | 2.80347 | 9.0 |
| 32.533 | 2.75005 | 6.6 |
| 43.447 | 2.08117 | 6.4 | is sufficiently stable that it retains these XRPD characteristics after 6 hours at 120° C. and/or after 6 months at about 40° C. and about 75% relative humidity; and is a solid in the form of free flowing crystals that are not needle shaped.

4. A process for the preparation of an $\alpha_2$ crystal form of Imatinib mesylate the process comprising:
  suspending Imatinib base in a solvent, the solvent comprising acetone, acetonitrile, a mixture of methanol and isopropanol, or a mixture of isopropanol and water;
  adding methane sulfonic acid to the resulting suspension at room temperature;
  maintaining the solution at the reflux temperature of the solvent or at room temperature; and
  filtering to obtain the $\alpha_2$ crystal form;
  wherein the $\alpha_2$ crystal form has the XRPD characteristics given below,

| Angle 2-Theta | d Value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |

-continued

| Angle 2-Theta | d Value Angstrom | Intensity % |
|---|---|---|
| 28.475 | 3.13204 | 42.4 |
| 31.896 | 2.80347 | 9.0 |
| 32.533 | 2.75005 | 6.6 |
| 43.447 | 2.08117 | 6.4 | is sufficiently stable that it retains these XRPD characteristics after 6 hours at 120° C. and/or after 6 months at about 40° C. and about 75% relative humidity; and is a solid in the form of free flowing crystals that are not needle shaped.

5. A pharmaceutical composition comprising:
  an excipient; and
  an $\alpha_2$ crystal form of Imatinib mesylate that has the XRPD characteristics given below,

| Angle 2-Theta | d Value Angstrom | Intensity % |
|---|---|---|
| 4.841 | 18.24057 | 33.6 |
| 10.410 | 8.49070 | 100.0 |
| 11.194 | 7.89775 | 14.2 |
| 11.856 | 7.45827 | 19.9 |
| 12.881 | 6.86709 | 6.8 |
| 13.819 | 6.40328 | 12.9 |
| 14.860 | 5.95663 | 67.7 |
| 16.439 | 5.38788 | 32.4 |
| 17.049 | 5.19665 | 5.6 |
| 17.623 | 5.02870 | 58.6 |
| 18.052 | 4.91000 | 61.6 |
| 18.567 | 4.77491 | 98.8 |
| 19.032 | 4.65925 | 70.2 |
| 19.772 | 4.48657 | 15.3 |
| 21.236 | 4.18055 | 60.8 |
| 21.582 | 4.11431 | 59.4 |
| 22.594 | 3.93217 | 19.7 |
| 23.137 | 3.84112 | 21.8 |
| 23.696 | 3.75172 | 25.0 |
| 24.851 | 3.57993 | 58.6 |
| 26.250 | 3.39226 | 9.1 |
| 27.341 | 3.25932 | 18.7 |
| 28.475 | 3.13204 | 42.4 |
| 31.896 | 2.80347 | 9.0 |
| 32.533 | 2.75005 | 6.6 |
| 43.447 | 2.08117 | 6.4 | is sufficiently stable that it retains these XRPD characteristics after 6 hours at 120° C. and/or after 6 months at about 40° C. and about 75% relative humidity; and is a solid in the form of free flowing crystals that are not needle shaped.

6. The pharmaceutical composition of claim 5, comprising 45 to 60 wt-% the $\alpha_2$ crystal form of Imatinib mesylate.

7. The pharmaceutical composition of claim 5, wherein the excipients comprises microcrystalline cellulose, XL, colloidal silicone dioxide, magnesium stearate, talc, or a mixture thereof.

* * * * *

UNITED STATES PATENT AND TRADEMARK OFFICE
CERTIFICATE OF CORRECTION

| | | |
|---|---|---|
| PATENT NO. | : 8,048,883 B2 | Page 1 of 1 |
| APPLICATION NO. | : 10/585702 | |
| DATED | : November 1, 2011 | |
| INVENTOR(S) | : Amala et al. | |

It is certified that error appears in the above-identified patent and that said Letters Patent is hereby corrected as shown below:

In the Specification

Col. 2, line 43: "resulted only in the α-form" should read --resulted only in the β-form--

Signed and Sealed this
Twenty-first Day of October, 2014

Michelle K. Lee
*Deputy Director of the United States Patent and Trademark Office*